United States Patent

Floreancig et al.

(10) Patent No.: US 11,738,088 B2
(45) Date of Patent: Aug. 29, 2023

(54) BORYL ETHERS, CARBONATES, AND CYCLIC ACETALS AS OXIDATIVELY-TRIGGERED DRUG DELIVERY VEHICLES

(71) Applicants: Paul E. Floreancig, Pittsburgh, PA (US); Alexander Deiters, Pittsburgh, PA (US); Ramsey D. Hanna, Falls Church, VA (US); Yuta R. Naro, Pittsburgh, PA (US)

(72) Inventors: Paul E. Floreancig, Pittsburgh, PA (US); Alexander Deiters, Pittsburgh, PA (US); Ramsey D. Hanna, Falls Church, VA (US); Yuta R. Naro, Skaneateles, NY (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1248 days.

(21) Appl. No.: 16/322,076

(22) PCT Filed: Jul. 28, 2017

(86) PCT No.: PCT/US2017/044465
§ 371 (c)(1),
(2) Date: Jan. 30, 2019

(87) PCT Pub. No.: WO2018/026656
PCT Pub. Date: Feb. 8, 2018

(65) Prior Publication Data
US 2019/0184022 A1    Jun. 20, 2019

Related U.S. Application Data

(60) Provisional application No. 62/369,596, filed on Aug. 1, 2016.

(51) Int. Cl.
| | |
|---|---|
| A61K 47/54 | (2017.01) |
| A61P 35/00 | (2006.01) |
| A61P 25/28 | (2006.01) |
| C07F 5/02 | (2006.01) |
| C01B 35/10 | (2006.01) |
| A61K 49/00 | (2006.01) |
| C07F 5/04 | (2006.01) |

(52) U.S. Cl.
CPC ........ *A61K 47/559* (2017.08); *A61K 49/0039* (2013.01); *A61K 49/0052* (2013.01); *A61P 25/28* (2018.01); *A61P 35/00* (2018.01); *C01B 35/10* (2013.01); *C07F 5/02* (2013.01); *C07F 5/025* (2013.01); *C07F 5/04* (2013.01)

(58) Field of Classification Search
None
See application file for complete search history.

(56) References Cited

U.S. PATENT DOCUMENTS

2011/0312905 A1* 12/2011 Cohen ............... A61P 9/00
536/4.1

FOREIGN PATENT DOCUMENTS

| JP | 2006-248938 | 9/2006 |
| WO | WO 2011/133800 | 10/2011 |
| WO | WO 2013/028371 | 2/2013 |

OTHER PUBLICATIONS

Anderson, K.A., et al., "Boronic Acid for the Traceless Delivery of Proteins into Cells", ACS Chem. Biol., pp. 319-323 (Year: 2015).*
Das, B.C., et al., "Boron chemicals in diagnosis and therapeutics", Future MEd. Chem., pp. 653-676 (Year: 2013).*
Hagan, H., et al., "Aminoferrocene-Based Prodrugs Activated by Reactive Oxygen Species", J. Med. Chem., pp. 924-934 (Year: 2012).*
Bao, Y., et al., "D-α-Tocopherol Polyethylene Glycol Succinate-Based RedoxSensitive Paclitaxel Prodrug for Overcoming Multidrug Resistance in Cancer Cells" Mol. Pharmaceutics, pp. 3196-3209 (Year: 2014).*
Ban, H.S., et al., "Discovery of boron-conjugated 4-anilinoquinazoline as a prolonged inhibitor of EGFR tyrosine kinase", Org. Biomol. Chem., pp. 4415-4427 (Year: 2009).*
Broaders et al., "A Biocompatible Oxidation-Triggered Carrier Polymer with Potential in Therapeutics," *JACS*, vol. 133, pp. 756-758, Dec. 20, 2010.
International Search Report and Written Opinion issued for International Application No. PCT/US2017/044465 dated Oct. 17, 2017.

(Continued)

*Primary Examiner* — Michael G. Hartley
*Assistant Examiner* — Lance W Rider
(74) *Attorney, Agent, or Firm* — Klarquist Sparkman, LLP

(57) ABSTRACT

A compound, or a pharmaceutically acceptable salt thereof, having a structure of:

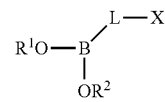

wherein L is a cleavable linker group;
X is a cargo moiety-containing group; and
$R^1$ and $R^2$ are each independently hydrogen, alkyl, or substituted alkyl; or $R^1$ and $R^2$ together form a boronic ester ring or a substituted boronic ester group.

27 Claims, 8 Drawing Sheets

(56) References Cited

OTHER PUBLICATIONS

Molander et al., "Stereospecific Cross-Coupling of Secondary Organotrifluoroborates: Potassium 1-(Benzyloxy)alkyltrifluoroborates," *JACS*, vol. 134, pp. 16856-16868, Oct. 1, 2012.
Mosey et al., "Versatile approach to alpha-alkoxy carbamate synthesis and stimulus-responsive alcohol release," *Organic & Biomolecular Chemistry*, 10(39): 7980-7985, Oct. 21, 2012.

* cited by examiner

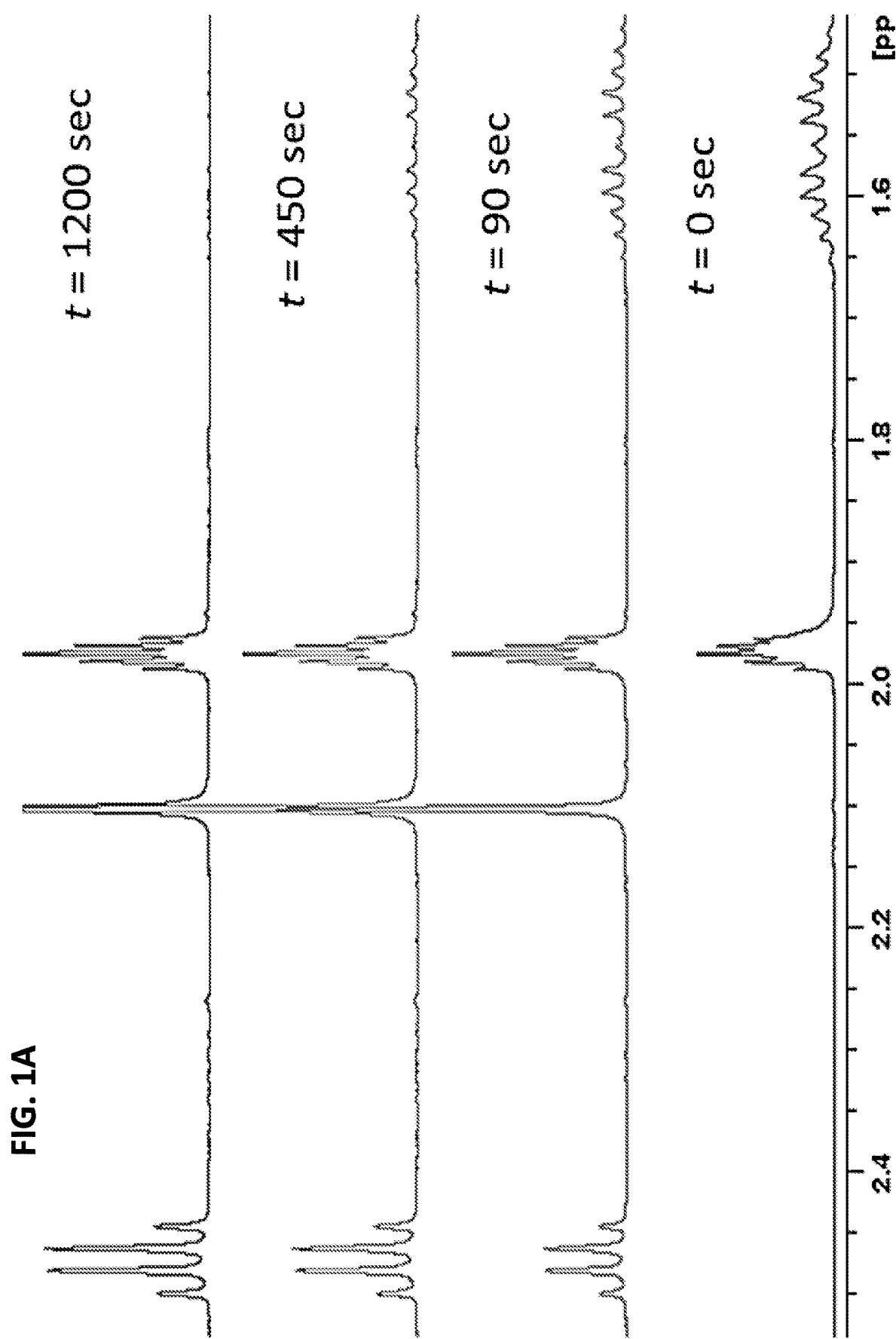

BORYL ETHERS, CARBONATES, AND CYCLIC ACETALS AS OXIDATIVELY-TRIGGERED DRUG DELIVERY VEHICLES

CROSS REFERENCE TO RELATED APPLICATIONS

This application is the U.S. National Stage of International Application No. PCT/US2017/044465, filed Jul. 28, 2017, which was published in English under PCT Article 21(2), which in turn claims the benefit of U.S. Provisional Application No. 62/369,596, filed Aug. 1, 2016, which is herein incorporated by reference in its entirety.

ACKNOWLEDGMENT OF GOVERNMENT SUPPORT

This invention was made with government support under grant number AI068021 awarded by the National Institutes of Health. The government has certain rights in the invention.

BACKGROUND

Reactive oxygen species (ROS), including hydrogen peroxide, are linked to a number of disparate medical conditions including neurological diseases, cancer, aging, and diabetes. ROS-rich environments are also created through exposure to ionizing radiation, as encountered in radiotherapy. Hydrogen peroxide's unique reactivity properties and importance in these conditions have resulted in its utilization to initiate a number of processes in biological and materials chemistry. $H_2O_2$ is an attractive agent for initiating prodrug unraveling in many cases because it is small and can access sterically hindered sites in structures that are inaccessible to enzymes, which are commonly utilized for this purpose.

Peroxide-mediated drug release has been explored to a limited extent. However substrates for these processes employ aryl or vinyl boronates as oxidative triggers to promote release from the benzylic or allylic position. Therapeutic applications of these systems, therefore, can be complicated by the significant toxicity of the resultant quinone methide or acrolein by-products. Thus alternative structural motifs that release compounds in the presence of $H_2O_2$ without generating toxic by-products would be valuable for applications in oxidative drug release.

SUMMARY

Disclosed herein in one embodiment is a compound, or a pharmaceutically acceptable salt thereof, having a structure of:

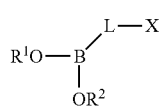

wherein L is a cleavable linker group;
X is a cargo moiety-containing group; and
$R^1$ and $R^2$ are each independently hydrogen, alkyl, or substituted alkyl; or $R^1$ and $R^2$ together form a boronic ester ring or a substituted boronic ester group.

Also disclosed herein is a method for treating a reactive oxygen species-mediated condition in a subject, comprising administering a therapeutically effective amount of a compound of any one of claims 1 to 15 to the subject in need thereof.

The foregoing will become more apparent from the following detailed description, which proceeds with reference to the accompanying figures.

BRIEF DESCRIPTION OF THE DRAWINGS

FIGS. 1A-B are graphs demonstrating the oxidative breakdown of compound 7. FIG. 1A shows the reaction progress as determined by NMR. FIG. 1B shows the reaction progress as a function of pH.

DETAILED DESCRIPTION

Terminology

Figure 1B:
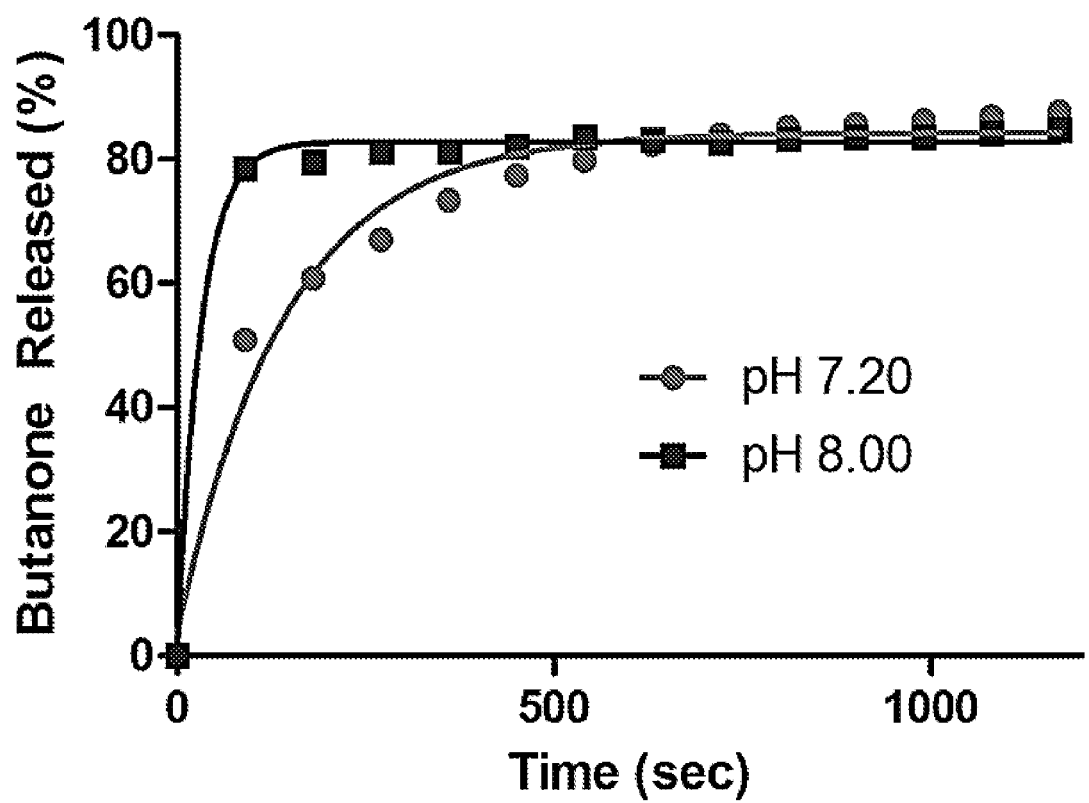

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

"Administration" as used herein is inclusive of administration by another person to the subject or self-administration by the subject.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical derived from aliphatic, cycloaliphatic, aryl, and alkanearyl hydrocarbons.

"Alkenyl" refers to a cyclic, branched or straight chain group containing only carbon and hydrogen, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "amine" or "amino" refers to a group of the formula —NRR', where R and R' can be, independently, hydrogen or an alkyl, alkenyl, alkynyl, acyl, aryl, aralkyl, cycloalkyl, halogenated alkyl, or heterocycloalkyl group. For example, an "alkylamino" or "alkylated amino" refers to —NRR', wherein at least one of R or R' is an alkyl. A suitable amine or amino group is acetamido.

The term "aminoalkyl" refers to alkyl groups as defined above where at least one hydrogen atom is replaced with an amino group (e.g, —$CH_2$—$NH_2$).

"Aminocarbonyl" alone or in combination, means an amino substituted carbonyl (carbamoyl) radical, wherein the amino radical may optionally be mono- or di-substituted, such as, for example, with alkyl, aryl, acyl, aralkyl, cycloalkyl, cycloalkylalkyl, alkanoyl, alkoxycarbonyl, aralkoxycarbonyl and the like. For example, an aminocarbonyl may be represented by the formula —C(O)NRR', where R and R' independently can be, for example, a hydrogen, alkyl, alkenyl, alkynyl, acyl, aryl, aralkyl, cycloalkyl, halogenated alkyl, or heterocycloalkyl group.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed rings (e.g., naphthyl or anthryl), which can optionally be unsubstituted or substituted. A "heteroaryl group," is defined as an aromatic group that has at least one heteroatom incorporated within the ring of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

A "carbonylamino" group may be —N(R)—C(O)—R (wherein each R is independently a substitution group such as, for example, alkyl, alkenyl, alkynyl, acyl, aryl, aralkyl, cycloalkyl, halogenated alkyl, or heterocycloalkyl group, or H). A suitable carbonylamino group is acetamido.

The term "carboxylate" or "carboxyl" refers to the group —COO$^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

The term "halogen" refers to F, Cl, Br or I.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$ alkyl, $C_{2-6}$alkenyl, $C_{2-6}$alkynyl, $C_{3-8}$ cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$ alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Thiol" refers to the group —SH.

The term "substituted thiol" refers to a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art.

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed compounds can have at least one asymmetric center or geometric center, cis-trans center (C=C, C=N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}$F, etc.

Compounds

Disclosed herein are compounds can be used to release active moieties in oxidatively stressed environments. Disease states that are characterized by oxidative stress include cancer, diabetes, and neurodegenerative conditions. Oxidative stress can also be amplified by radiation. In certain embodiments, the releasable active moiety is a bioactive moiety such as a therapeutically active moiety. In certain embodiments, the releasable active moiety is a detectable moiety, for example, a fluorophore.

The compounds release the active moiety upon reaction with a reactive oxygen species (ROS), for example, hydrogen peroxide. In certain embodiments, the compounds are prodrugs that release the active moiety in vivo upon reaction with a reactive oxygen species, for example, hydrogen peroxide.

The compounds can be functionalized to incorporate functional groups that target a biological structure such as, for example, a cell.

In certain embodiments, the by-products of the active moiety release are non-toxic. In particular, the compounds disclosed herein avoid the release of toxic quinone methides or acroleins that are generated upon the breakdown of other peroxide-sensitive prodrugs. Rather, the compounds disclosed herein release alcohols, ketones or aldehydes under oxidative conditions.

The release rates can be adjusted by structural manipulations. For example, attaching the active moiety to the boryl moiety via a carbonate linker can slow down the release rate.

α-Boryl ethers, carbonates, and acetals as disclosed herein in certain embodiments, are readily prepared from the corresponding alcohols that are accessed through ketone diboration, and react rapidly with hydrogen peroxide to release alcohols, aldehydes, and ketones through the collapse of hemiacetal intermediates.

The compounds disclosed herein are readily accessible structures that have the capacity to localize toward a cellular target and decompose under oxidative conditions to release a biological effector. A prior design for alcohol release (Mosey et al, Org. Biomol. Chem. 2012, 10, 7980; see Scheme 1) employed acyl aminal substrates (1) that are available through reductive multicomponent unions of nitriles, chloroformates, and alcohols. Aryl or vinyl boronate oxidation with $H_2O_2$ releases a quinone methide or acrolein and $CO_2$ to form an unstable hemiaminal (2) that collapses to release the alcohol. We reasoned that oxidation of α-boryl ethers or carbonates (3) would provide a similar unstable hemiacetal (4) that releases an alcohol directly or through carbonate breakdown with less by-product generation. This approach allows for the selection of a non-toxic ketone by-product to serve as a guide in substrate design.

Scheme 1. Alcohol release through boronate oxidation.

Prior studies

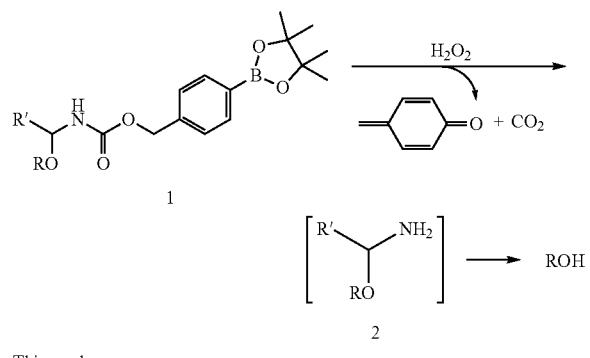

This work

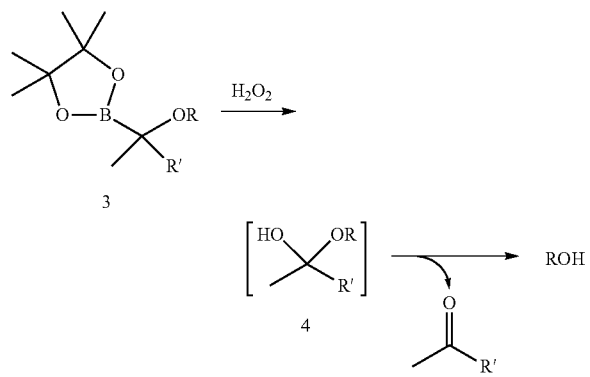

Disclosed herein is a scaffold that can release several diverse structures via oxidative fragmentation of α-boryl ethers, carbonates, and acetals. Specific advances include 1) the development of experimentally facile conditions for the synthesis of α-boryl alcohols through a variant of a known ketone diboration protocol, 2) the preparation of α-boryl ethers and carbonates through conditions that avoid strong base, 3) the demonstration that α-boryl ethers decompose rapidly and efficiently in the presence of $H_2O_2$ under mildly basic conditions while α-boryl carbonates decompose more slowly, 4) the elaboration of several protocols for preparing cyclic boryl-substituted acetals, 5) the observation that the acetals can liberate aldehydes and ketones in the presence of $H_2O_2$, 6) the application of the acetal breakdown to release fluorophores at low substrate and peroxide concentrations, 7) the validation of the capacity of the acetals to release cargo in cells through stimulation with exogenous $H_2O_2$, and 8) the demonstration that cargo can be released in cells by endogenous $H_2O_2$ resulting from chemically stimulated oxidative stress. These results clearly illustrate that α-boryl ethers, carbonates, and acetals are viable substrates for releasing biological effectors in cells in response to oxidative conditions while avoiding the generation of toxic by-products.

In certain embodiments, the compounds are substantially non-toxic to a living cell, and thus are suitable for reacting with an ROS in a living cell (in vivo, ex vivo, or in vitro), in the extracellular medium in which a living cell is cultured in vitro or ex vivo, or extracellularly in a multicellular organism. ROS include oxygen related free radicals such as superoxide ($O_2-$), peroxyl (ROO—), alkoxyl (RO—), hydroxyl (HO—), and nitric oxide; and non-radical species, such as hydrogen peroxide ($H_2O_2$), hypochlorous acid, singlet oxygen, alkoxides, hydroxide, and peroxynitrite.

In certain embodiments, the compound selectively reacts with hydrogen peroxide, compared to other ROS. In some embodiments, a subject compound reacts with hydrogen peroxide, and does not substantially react with ROS other than hydrogen peroxide, e.g., the compound does not substantially react with any of superoxide anion, nitric oxide, peroxyl radical, alkoxyl radical, hydroxyl radical, hypochlorous acid, and singlet oxygen.

In certain embodiments, the compound reacts (and cleaves) with endogenous hydrogen peroxide. In certain embodiments, the compound reacts (and cleaves) with exogenous hydrogen peroxide (e.g., hydrogen peroxide generated by a hydrogen peroxide inducer administered to a subject). In certain embodiments, the compound reacts (and cleaves) with endogenous hydrogen peroxide and exogenous hydrogen peroxide. In certain embodiments, the hydrogen peroxide can be induced by administering radiation to the subject (e.g., cancer radiotherapy).

In certain embodiments, the compounds are self-immolative, e.g., compounds that respond to an external stimulus (e.g., a reactive oxygen species) to undergo a fragmentation or cleavage to release an active moiety.

In particular, disclosed herein are compounds, or a pharmaceutically acceptable salt thereof, having a structure of:

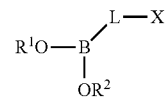

wherein L is a cleavable linker group;

X is a cargo moiety-containing group; and $R^1$ and $R^2$ are each independently hydrogen, alkyl, or substituted alkyl; or $R^1$ and $R^2$ together form a boronic ester ring or a substituted boronic ester group.

$R^1$ and $R^2$ can each be independently selected from hydrogen, alkyl, or substituted alkyl; or $R^1$ and $R^2$ together can form a boronic ester ring or substituted boronic ester ring. In certain embodiments, both $R^1$ and $R^2$ are hydrogen. In certain embodiments, both $R^1$ and $R^2$ are alkyl, such as, for example, methyl, ethyl, propyl, isopropyl, and butyl. In certain embodiments, $R^1$ and $R^2$ together form a boronic ester ring or substituted boronic ester ring. In certain embodiments, R1 and R2 together form a boronic ester ring. In certain embodiments, $R^1$ and $R^2$ together form a substituted boronic ester ring. In certain embodiments, the —B($OR^1$)($OR^2$) group is selected from the following:

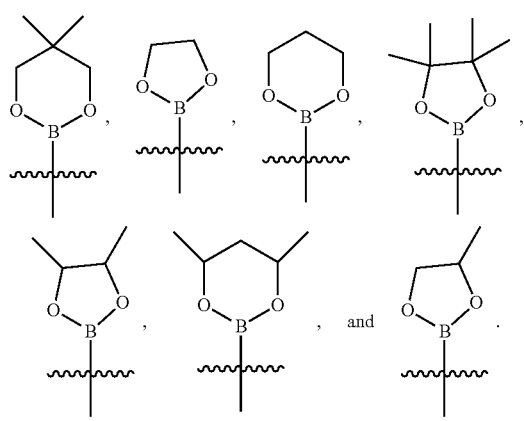

The cleavable linker group is a linker that can be selectively cleaved to produce two products. Application of suitable cleavage conditions to a molecule containing a cleavable linker that is cleaved by the cleavage conditions will produce at least two by-products. A cleavable linker is stable, e.g. to physiological conditions, until the molecule is contacted with a cleavage-inducing stimulus, such as a cleavage-inducing agent (e.g., a reactive oxygen species). L is a cleavable linker group that provides for release of X upon reaction of the —B(OR$^1$)(OR$^2$) group with a reactive oxygen species, where release of X includes cleavage of the cleavable B—C bond.

In certain embodiments, L includes an —O—, —C(O)—, or —O—C(O)—O—.

In certain embodiments, —B-L- together form a boryl ether, boryl carbonate or boryl cyclic acetal.

In certain embodiments, L is selected from:

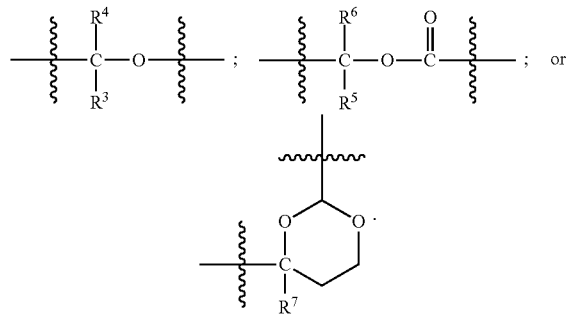

wherein R$^3$-R$^7$ are each independently selected from hydrogen, alkyl, substituted alkyl, thiol or substituted thiol, or a targeting moiety as described below. In certain embodiments, R$^3$-R$^7$ are each independently selected from (C$_1$-C$_6$) alkyl or substituted (C$_1$-C$_6$)alkyl.

X is a cargo moiety-containing group. In certain embodiments, the cargo moiety may be an active moiety such as a bioactive moiety, for example, a therapeutically active moiety. In certain embodiments, the active moiety is a detectable moiety, for example, a fluorophore moiety. In certain embodiments, X may include both a therapeutically active moiety and a detectable moiety.

Illustrative therapeutically active moieties include anticancer agents, neurological agents, or antioxidants. Illustrative anticancer agents include a nitrogen mustard (e.g., mechlorethamine, cyclophosphamide, melphalan, chlorambucil), an alkyl sulfonate (e.g., busulfan), a nitrosourea (e.g., carmustine and lomustine), a triazine (e.g., dacarbazine and temozolomide), a platinum drug (e.g., carboplatin and cisplatin), and combinations thereof. In other embodiments, the anticancer agent may be a DNA cleaving agent such as bleomycin. In further embodiments, the anticancer agent may be a DNA oxidizing agent that directly or indirectly generates lesions for base excision repair such as an anthracycline (e.g., daunorubicin, doxorubicin, epirubicin). In further embodiments, the anticancer agent may be a recombination agent (e.g., trastuzumab). In additional embodiments, the anticancer agent may be a kinase inhibitor (e.g, vemurafenib), a cell cycle inhibitor, or a poly ADP ribose polymerase (PARP) inhibitor.

Illustrative anticancer agents include paclitaxel, doxorubicin, pederin, pederin analogs (such as those disclosed in Balachandran et al, J. Am. Chem. Soc. 2011, 133, 16668, which is incorporated herein by reference), theopederin D, psymberin, methotrexate, 5-fluorouracil, camptothecin, cisplatin, carboplatin, oxaliplatin, DACH-Pt, melphalan, chlorambucil, thiotepa, busulfan, etoposide, vinblastine, podophyllotoxin, colchicine, taxol, hydroxyurea, 5-azacytidine, capecitabine, imatinib, erlotinib, irinotecan, artemisole, sorafenib, sunitinib, trastuzumab, cyclophosphamide, bleomycin, vincristine, mitomycin, predisone), an EGF-receptor antagonist, arsenic sulfide, adriamycin, cimetidine, caminomycin, mechlorethamine hydrochloride, pentamethylmelamine, teniposide, chlorambucil, demethoxyhypocrellin A, melphalan, ifosfamide, trofosfamide, Treosulfan, podophyllotoxin or podophyllotoxin derivatives, etoposide phosphate, teniposide, leurosidine, leurosine, vindesine, 9-aminocamptothecin, camptoirinotecan, crisnatol, megestrol, methopterin, ecteinascidin 743, busulfan, carmustine, lomustine, lovastatin, 1-methyl-4-phenylpyridinium ion, semustine, staurosporine, streptozocin, phthalocyanine, dacarbazine, aminopterin, trimetrexate, thioguanine, mercaptopurine, fludarabine, pentastatin, cladribin, cytarabine, porfiromycin, 5-fluorouracil, 6-mercaptopurine, doxorubicin hydrochloride, leucovorin, mycophenolic acid, daunorubicin, deferoxamine, floxuridine, doxifluridine, raltitrexed, idarubicin, epirubican, pirarubican, zorubicin, mitoxantrone, bleomycin sulfate, actinomycin D, safracins, saframycins, quinocarcins, discodermolides, vinorelbine tartrate, vertoporfin, tamoxifen, raloxifene, tiazofuran, thioguanine, ribavirin, EICAR, estramustine, estramustine phosphate sodium, flutamide, bicalutamide, buserelin, leuprolide, pteridines, enediynes, levamisole, aflacon, interferon, interleukins, aldesleukin, filgrastim, sargramostim, rituximab, BCG, tretinoin, betamethasone, gemcitabine hydrochloride, verapamil, VP-16, altretamine, thapsigargin, oxaliplatin, iproplatin, tetraplatin, lobaplatin, DCP, PLD-147, JM118, JM216, JM335, satraplatin, docetaxel, deoxygenated paclitaxel, TL-139, 5'-nor-anhydrovinblastine, irinotecan, topotecan, BAY 38-3441, 9-nitrocamptothecin, exatecan, lurtotecan, gimatecan, homocamptothecins diflomotecan and 9-aminocamptothecin, SN-38, ST 1481, karanitecin, indolocarbazoles, protoberberines, intoplicines, idenoisoquinolones, benzo-phenazines and NB-506.

Illustrative neurological agents include vitamin E, coenzyme Q analogs, and neuroprotective terpenes such as achillolide A.

Illustrative detectable moieties include radioisotopes (such as $^{18}$F, $^{11}$C, $^{64}$Cu$^{2+}$ and $^{111}$In$^{3+}$) for PET and SPECT, supermagnetic (such as iron oxide) or paramagnetic (such as gadolinium) metals for MRI, fluorophores (such as dyes, quantum dots and nanoparticles) for optical and/or photoacoustic imaging, microbubbles for ultrasound and iodine for CT.

In certain embodiments, the cargo moiety may be, or include, a substituted or unsubstituted alkoxy, a substituted or unsubstituted aryl, a substituted or unsubstituted cycloalkyl, or a substituted or unsubstituted heterocycle (e.g., a heteroaryl or a heterocycloalkyl).

The cargo moiety-containing group may be conjugated to the cleavable linker group. In certain embodiments, there are reactive groups on the cargo moiety that serve as conjugation sites. For example, the cargo moiety may be functionalized with an alkyl halide, carbonyl, or chloroformate group that reacts with the linker. In certain embodiments, the conjugation site on the cargo moiety is an active site (e.g., a biologically active site) that is blocked via the conjugation to the linker. Upon cleavage by the ROS (e.g., hydrogen peroxide), the active site becomes available. The oxygen of the released cargo usually comes from the linker through a displacement of a —CH2X group, where X is a halogen or from an aldehyde or ketone.

U.S. Pat. No. 9,364,555, which is incorporated herein by reference, discloses pederin, pederin analogs, psymberin, and psymberin analogs as therapeutically agents that can be functionalized for conjugation and use in the presently disclosed compounds.

X and/or L may also include a moiety targeting a biological structure such as a cell. The targeting moiety binds, in certain embodiments selectively binds, to a binding partner (i.e. the target of interest). A binding partner may be a molecule or particle which is bound by the targeting moiety. It can be a cell, virus, fragment of a cell, antibody, fragment of an antibody, peptide, protein, polynucleotide, antigen, small molecule, or a combination thereof. Illustrative targeting moieties include receptor ligands, peptides, proteins, antibodies, antibody fragments and nucleic acids. The targeting moiety assists in selectively directing the compound to a desired target such as cancer tissue. For example, a targeting moiety may include a ligand for receptors that are present on cancer cells. Illustrative ligands include tamoxifen derivatives and sigma 2 receptor ligands.

The targeting moiety may be of any kind presently known, or that become known and includes peptides and non-peptides. Generally, these can be antibodies (especially monoclonal antibodies), lymphokines, hormones, growth factors, vitamins, nutrient-transport molecules (such as transferrin), or any other cell-binding molecule or substance. More specific examples of targeting moieties that can be used include: polyclonal antibodies; monoclonal antibodies; fragments of antibodies such as Fab, Fab', and F(ab').sub.2, Fv (Parham, J. Immunol. 131:2895-2902 (1983); Spring et al. J. Immunol. 113:470-478 (1974); Nisonoff et al. Arch. Biochem. Biophys. 89:230-244 (1960)); liposomes; dendrimers; interferons (e.g. alpha., .beta., gamma.); lymphokines such as IL-2, IL-3, IL-4, IL-6; hormones such as insulin, TRH (thyrotropin releasing hormone), MSH (melanocyte-stimulating hormone), steroid hormones, such as androgens and estrogens; growth factors and colony-stimulating factors such as EGF, TGF-alpha, FGF, VEGF, G-CSF, M-CSF and GM-CSF (Burgess, Immunology Today 5:155-158 (1984)); transferrin (O'Keefe et al. J. Biol. Chem. 260:932-937 (1985)); and vitamins, such as folate.

In one embodiment, the antibody-drug conjugate includes an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies can be used for the treatment of the disease with which the target antigen is associated. Non-limiting examples of target antigens (and their associated diseases) to which an antibody-linker-drug conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD80 (psoriasis), CD23 (asthma), CD40L (immune thrombocytopenic purpura), CTLA4 (T cell lymphomas) and BLys (autoimmune diseases, including systemic lupus erythematosus).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in MONOCLONAL ANTIBODIES AND CANCER THERAPY, Alan R. Liss, Inc. (1985)). Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, Eur. J. Immunol. 6: 511-519 (1976)). Alternative methods of immortalization include transformation with Epstein Barr Virus, oncogenes, or retroviruses, or other methods well known in the art.

In certain embodiments, the antibody is a chimeric or humanized antibody. Chimeric or humanized antibodies can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In another embodiment, the antibody is a human antibody. Such human antibodies can be generated by immunizing transgenic or transchromosomic mice in which the endogenous mouse immunoglobulin genes have been inactivated and exogenous human immunoglobulin genes have been introduced. Such mice are known in the art (see e.g., U.S. Pat. Nos. 5,545,806; 5,569,825; 5,625,126; 5,633,425;

5,789,650; 5,877,397; 5,661,016; 5,814,318; 5,874,299; and 5,770,429; all to Lonberg and Kay; U.S. Pat. Nos. 5,939,598; 6,075,181; 6,114,598; 6,150,584 and 6,162,963 to Kucherlapati et al.; and PCT Publication WO 02/43478 to Ishida et al.) Human antibodies can also be prepared using phage display methods for screening libraries of human immunoglobulin genes. Such phage display methods for isolating human antibodies also are known in the art (see e.g., U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.).

The antibody of the antibody-drug conjugates (ADCs) disclosed herein may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab). The antibody may be an antibody fragment, e.g. a Fab fragment.

Known antibodies for the treatment or prevention of cancer can be conjugated as ADC. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody for the treatment of patients with metastatic breast cancer; RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG.sub.2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG.sub.1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., et al Science (1993) 261, 212-215), BR64 (Trail, PA, et al Cancer Research (1997) 57, 100-105, mAbs against the CD40 antigen, such as S2C6 mAb (Francisco, J. A., et al Cancer Res. (2000) 60:3225-3231), mAbs against the CD70 antigen, such as 1F6 mAb, and mAbs against the CD30 antigen, such as AC10 (Bowen, M. A., et al (1993) J. Immunol., 151:5896-5906; Wahl et al., 2002 Cancer Res. 62 (13):3736-42). Many other internalizing antibodies that bind to tumor associated antigens can be used and have been reviewed (Franke, A. E., et al Cancer Biother Radiopharm. (2000) 15:459-76; Murray, J. L., (2000) Semin Oncol., 27:64-70; Breitling, F., and Dubel, S., Recombinant Antibodies, John Wiley, and Sons, New York, 1998).

Molecular targets for the antibody drug conjugates (ADC) include: (i) tumor-associated antigens; (ii) cell surface receptors, (iii) CD proteins and their ligands, such as CD3, CD4, CD8, CD19, CD20, CD22, CD34, CD40, CD79a and CD79ϵ; (iv) members of the ErbB receptor family such as the EGF receptor, HER2, HER3 or HER4 receptor; (v) cell adhesion molecules such as LFA-1, Mac1, p150,95, VLA-4, ICAM-1, VCAM and αv/β3 integrin including either alpha or beta subunits thereof (e.g. anti-CD11a, anti-CD18 or anti-CD11b antibodies); and (vi) growth factors such as VEGF; IgE; blood group antigens; flk2/flt3 receptor; obesity (OB) receptor; mp1 receptor; CTLA-4; protein C, BR3, c-met, tissue factor, β7 etc.

Additional targeting moieties, particularly for use with neurological agents, include groups that can penetrate the blood brain barrier, such as glucose or various peptides.

Compositions and Methods of Use

In certain embodiments, the compounds disclosed herein may be useful for treating any type of neoplasm (e.g., cancer). Neoplasms treatable by the presently disclosed compounds include all solid tumors, i.e., carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcoma broadly includes tumors whose cells are embedded in a fibrillar or homogeneous substance like embryonic connective tissue.

A solid tumor can be malignant, e.g. tending to metastasize and being life threatening, or benign. Examples of solid tumors that can be treated include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

Illustrative cancers also include blood-borne cancers such as leukemia, myeloma, or lymphoma.

Moreover, tumors comprising dysproliferative changes (such as metaplasias and dysplasias) are treated or prevented in epithelial tissues such as those in the cervix, esophagus, and lung. Thus, the presently disclosed methods provide for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

In certain embodiments, the presently disclosed methods are directed to a method for inhibiting cancer growth, including processes of cellular proliferation, invasiveness, and metastasis in biological systems. Preferably, the method is employed to inhibit or reduce cancer cell proliferation, invasiveness, metastasis, or tumor incidence in living animals, such as mammals.

Also provided herein is a method of inducing cytotoxicity (cell killing) in cancer cells or reducing the viability of cancer cells. For example, the compounds disclosed herein can be used to induce cytotoxicity in cells of carcinomas of the prostate, breast, ovary, testis, lung, colon, or pancreas.

In certain embodiments, the compounds disclosed herein may be administered to a subject in need thereof for treating a neurodegenerative disease or disorder such as, for example, Alzheimer's disease, ataxia telangiectasia, Parkinson's disease, amyotrophic lateral sclerosis, motor neuron disease, macular degeneration, glaucoma, and Huntington's disease.

The compounds of the invention may be useful in neuroprotection and in the treatment of neurodegeneration following stroke, cardiac arrest, pulmonary bypass, traumatic brain injury, spinal cord injury or the like.

In some embodiments, the methods disclosed herein involve administering to a subject in need of treatment a pharmaceutical composition, for example a composition that includes a pharmaceutically acceptable carrier and a therapeutically effective amount of one or more of the compounds disclosed herein. The compounds may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The compounds are preferably formulated into suitable pharmaceutical preparations such as tablets, capsules, or elixirs for oral administration or in sterile solutions or suspensions for parenteral administration. Typically the compounds described above are formulated into pharmaceutical compositions using techniques and procedures well known in the art.

In some embodiments, one or more of the disclosed compounds are mixed or combined with a suitable pharmaceutically acceptable carrier to prepare a pharmaceutical composition. Pharmaceutical carriers or vehicles suitable for administration of the compounds provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., $21^{st}$ Edition (2005), describes exemplary compositions and formulations suitable for pharmaceutical delivery of the compounds disclosed herein. In addition, the compounds may be formulated as the sole pharmaceutically active ingredient in the composition or may be combined with other active ingredients.

Upon mixing or addition of the compound(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts or prodrugs may also be used in formulating effective pharmaceutical compositions. The disclosed compounds may also be prepared with carriers that protect them against rapid elimination from the body, such as time-release formulations or coatings. Such carriers include controlled release formulations, such as, but not limited to, microencapsulated delivery systems.

The disclosed compounds and/or compositions can be enclosed in multiple or single dose containers. The compounds and/or compositions can also be provided in kits, for example, including component parts that can be assembled for use. For example, one or more of the disclosed compounds may be provided in a lyophilized form and a suitable diluent may be provided as separated components for combination prior to use. A kit may include a plurality of containers, each container holding one or more unit dose of the compound. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The pharmaceutical compositions may be in a dosage unit form such as an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

The compound is included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems for the treated disorder. In some examples, a therapeutically effective amount of the compound is an amount that lessens or ameliorates at least one symptom of the disorder for which the compound is administered. Typically, the compositions are formulated for single dosage administration. The concentration of active compound in the drug composition will depend on absorption, inactivation, and excretion rates of the active compound, the dosage schedule, and amount administered as well as other factors known to those of skill in the art.

In some examples, about 0.1 mg to 1000 mg of a disclosed compound, a mixture of such compounds, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more compounds. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed compound(s).

The disclosed compounds or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the compound is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the subject 1, 2, 3, 4, or more times daily. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the compounds can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The compounds can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The compounds can also be administered sublingually. When given sublingually, the compounds should be given one to four times daily in the amounts described above for IM administration.

The compounds can also be administered intranasally. When given by this route, the appropriate dosage forms are a nasal spray or dry powder. The dosage of the compounds for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The compounds can be administered intrathecally. When given by this route, the appropriate dosage form can be a parenteral dosage form. The dosage of the compounds for intrathecal administration is the amount described above for IM administration.

The compounds can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The compounds can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

The compounds disclosed herein may be co-administered with non-chemotherapeutic treatment methods. Examples of such methods include, but are not limited to, surgery, thermoablation, radiation, etc. or a combination of those methods.

It should be apparent to one skilled in the art that the exact dosage and frequency of administration will depend on the particular compounds administered, the particular condition being treated, the severity of the condition being treated, the age, weight, general physical condition of the particular subject, and other medication the individual may be taking as is well known to administering physicians or other clinicians who are skilled in therapy of retroviral infections, diseases, and associated disorders.

Examples

Ether, Carbonate, and Cyclic Acetal Substrate Synthesis and Decomposition.

We initially employed Clark's ketone-relevant variation of the Sadighi carbonyl diboration protocol for the conversion of 5 to boryl alcohol 6 (Scheme 2). These conditions (PinB-BPin, (ICy)CuCl, NaOtBu, PhMe, 50° C. followed by borate protodeboration on silica gel) provided 6, but were deemed to be unacceptable due to the low reaction rate and because of the technical difficulty associated with the need to initiate the reaction in a glove box. We reasoned that the relevant copper carbene catalyst could be prepared in situ by deprotonating the imidazolium salt in the presence of CuCl, thereby obviating the need to isolate this sensitive species.

Moreover adding MeOH to the reaction mixture substantially increased the rate of the reaction, in accord with Molander's observations. These changes resulted in the conversion of 5 to 6 in 92% yield within 1 h and without recourse to glove box or Schlenk line techniques. The experimental facility of this protocol appreciably enhances access to α-boryl alcohols. This is significant because boronates and related species with α-heteroatom substitution are useful as substrates for cross-coupling and chain elongation reactions, and as surrogates of functionalized carboxylic acids for applications in medicinal chemistry. The hydroxy groups can be functionalized readily, as demonstrated through the formation of methoxymethyl ether 7 and phenyl carbonate 8.

Scheme 2. α-Boryl alcohol synthesis and functionalization.

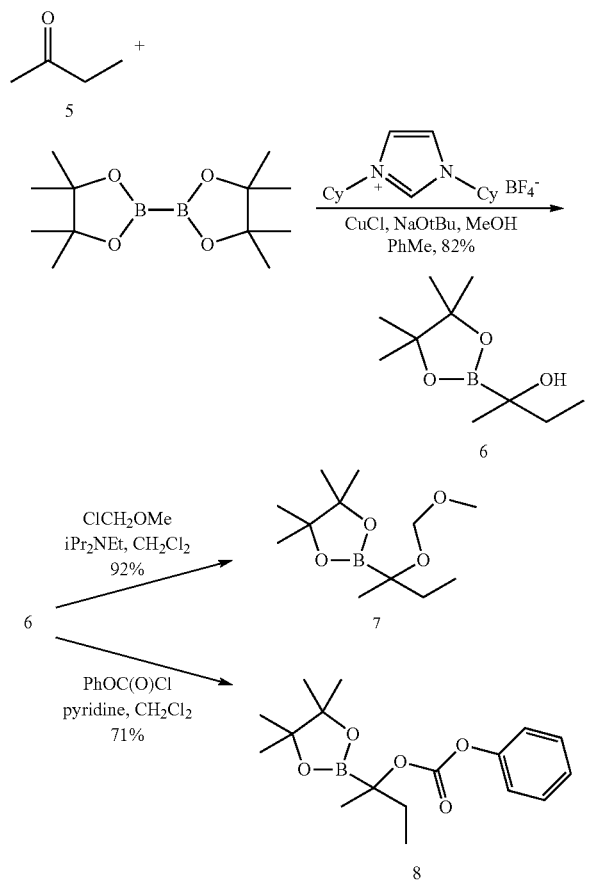

The oxidative breakdown of compounds 7 and 8 was achieved by subjecting them (~25 mM) to urea.$H_2O_2$ (300 mM) in a mixture of $CD_3CN$ and aqueous ($D_2O$) buffer (pH=8.0). The buffer was selected to mimic the experimentally determined pH of mitochondria in consideration of potential applications to mitigating neuronal oxidative stress. Initial experiments were conducted in a 5:1 ratio of $CD_3CN$ and buffer (Scheme 3). Reaction progress was monitored by $^1$H NMR through following the disappearance of the signals for diastereotopic hydrogens from the methylene group in the starting materials and the appearance of the corresponding enantiotopic hydrogens in butanone. Conversions were calculated by comparison to the internal standard 1,2-dimethoxyethane.

Scheme 3. Oxidative alcohol release.

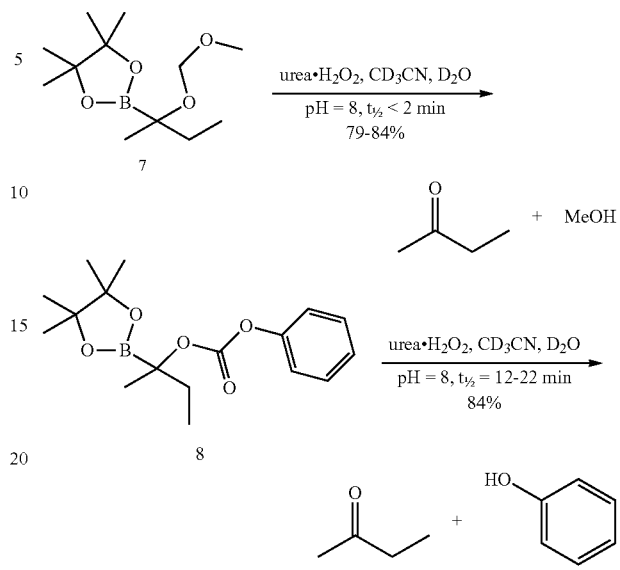

Methoxymethyl ether 7 fragmented quite rapidly in the presence of hydrogen peroxide. Over 50% of the starting material was consumed in less than 2 minutes (FIG. 1A), and complete conversion was observed within 20 mM with a 79% NMR yield of butanone. Changing the solvent to a 1:1 ratio of $CD_3CN$ to buffer did not slow the reaction and resulted in a slightly increased NMR yield of 84%. Moreover lowering the pH to a cytosolic-relevant value of 7.2 had only a minimal effect on the rate despite the diminished peroxy anion concentration (FIG. 1B), providing an 81% NMR yield of butanone.

Carbonate 8, however, broke down much more slowly under the oxidative conditions. Consumption of 50% of the starting material required 22 min when the reaction was conducted in a 5:1 mixture of $CD_3CN$ and buffer. Changing the solvent to a 1:1 mixture of $CD_3CN$ and buffer resulted in a slightly increased rate, with 50% of the starting material being consumed within 12 min. The reactions were quite efficient, with both providing an 84% yield of the desired products.

Figure 2:
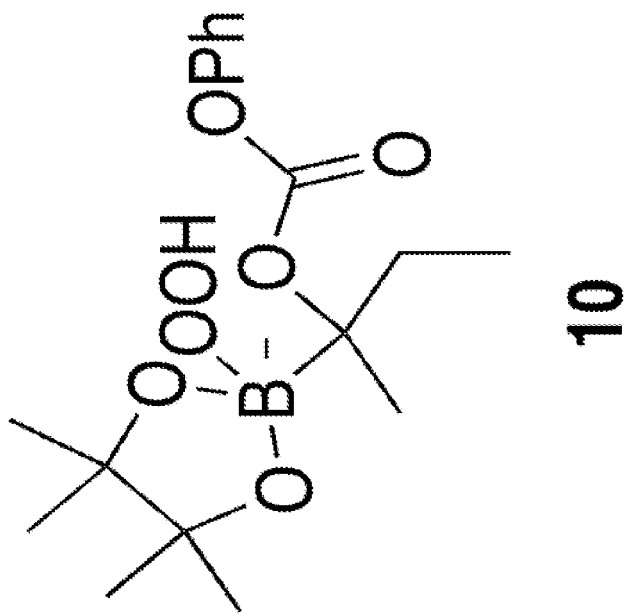
FIG. 2 shows the structures 9 and 10 as potential origins for the slow breakdown of 8.
Figure 2:
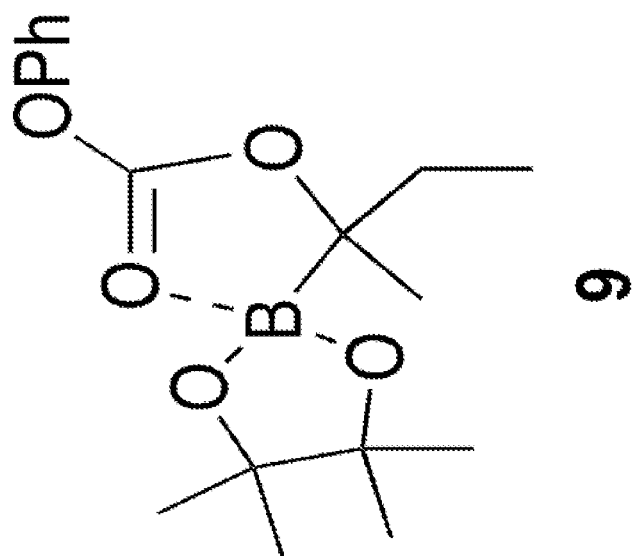

The rate difference for alcohol release between acetal and carbonate substrates indicates that the rate determining step in these processes is boronate oxidation rather than hemiacetal collapse. The slow breakdown of the carbonate could result from intramolecular coordination between the carbonyl oxygen and the boron, as illustrated by 9 (FIG. 2) thereby inhibiting the approach of HOO⁻ to the boron. Crystal structures show this type of coordination in α-boryl amides, and intramolecular coordination has been shown to confer stability to boronates. However the $^{11}$B chemical shift of 8 (δ 32.2 ppm) is nearly identical to the $^{11}$B chemical shift in 7 (δ 32.1 ppm), and is significantly different from amido pinacolboronates, which show $^{11}$B chemical shifts of approximately 15 ppm. Alternatively the breakdown could be slowed by a diminished migratory aptitude resulting from the presence of an electron withdrawing acyl group. No evidence of a persistent peroxyboronate intermediate, such as 10, was observed upon monitoring the progress of the reaction with $^{11}$B NMR, however. Regardless of the origin of the effect, the capacity to control the breakdown rate through a simple structural modification provides kinetic versatility in drug release strategy. Several additional substrates were prepared to define the scope of the process (Table 1). Secondary alcohols such as cyclohexanol (from the breakdown of 11) and the more complex menthol (from the breakdown of 13) are released smoothly. Although the formation and fragmentation of alkoxymethyl ethers proceeds rapidly and smoothly, direct release of alcohols would be desirable for avoiding the generation of toxic formaldehyde, particularly if the cargo is not intended to effect a cytotoxic response. Primary and secondary alcohols can be released directly, as shown in entries 3-5. The use of an aldehyde-derived boronate in entry 5 facilitated the synthesis of the ether. The oxidative cleavage of 15 and 20 (entries 3 and 6) are also significant because they show that functionalized substrates participate well in this process, providing potential handles for incorporating tissue-, cell-, or organelle-targeting functional groups. Boronate 20 releases the antioxidant pentamethyl chromanol (21), showing that this method could be applied to the release of radical scavengers in the presence of environments that are rich in reactive oxygen species, such as mitochondria. As previously discussed, this release was predictably somewhat slow due to the carbonate linker. The release of carboxylic acids (entry 7), while possible, is substantially slower than the release of alcohols or carbonates and is therefore not likely to be useful. Compound 22 showed a chemical shift of 27.0 ppm in the $^{11}$B NMR spectrum, indicating that coordination between the boron and the carbonyl group is likely to play a role in preventing oxidative cleavage through peroxide attack.

TABLE 1

Alcohol release scope.[a]

| entry | substrate[b] | product | $t_{1/2}$ (min)[c] | yield (%)[d] |
|---|---|---|---|---|
| 1 | 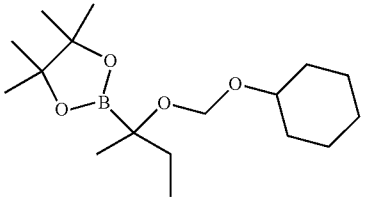 11 | 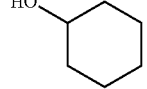 12 | <2 | 84 |
| 2 | 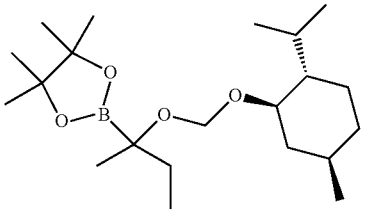 13 | 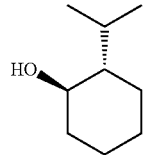 14 | <2 | 85 |
| 3 | 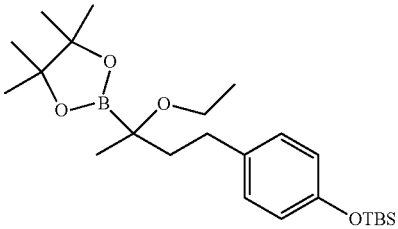 15 | 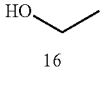 16 | <2 | 89 |
| 4 | 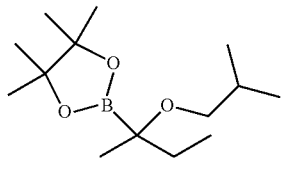 17 | 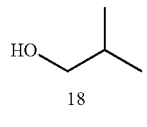 18 | <2 | 89 |

TABLE 1-continued

Alcohol release scope.[a]

| entry | substrate[b] | product | $t_{1/2}$ (min)[c] | yield (%)[d] |
|---|---|---|---|---|
| 5 | 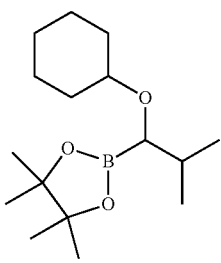 19 | 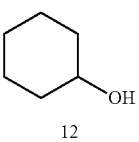 12 | <2 | 83 |
| 6 | 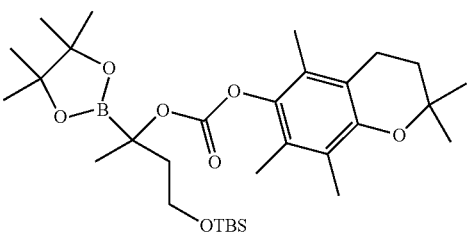 20 | 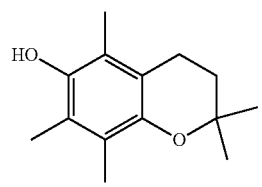 21 | 90 | 79 |
| 7 | 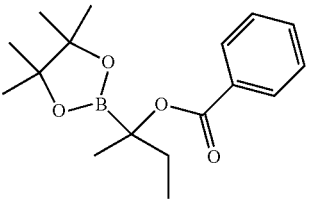 22 | 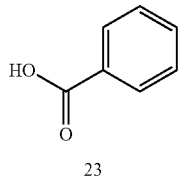 23 | >936 | 16 |

[a]Reactions run with 6-12 equiv H$_2$O$_2$•urea at pH = 8.0 in CD$_3$CN and D$_2$O (5:1) at rt.
[b]See the Supporting Information for the preparation of the substrates.
[c]As determined by monitoring substrate consumption.
[d]Determined by 1H NMR through comparing to the internal standard 1,2-dimethoxyethane.

The synthesis of alkyl ethers is challenging in comparison to the synthesis of alkoxymethyl ethers because direct Williamson ether syntheses with α-boryl alcohols are prone to undergo bora-Brook rearrangements that render the oxygen non-nucleophilic. Direct etherification requires sufficiently potent electrophiles to subvert the need for alkoxide generation. This can be achieved (Scheme 4) by activating halide leaving groups with AgOTf, allowing for hindered pyridines to be used as proton scavengers. This is illustrated by the ethylation of α-boryl alcohol 24 to yield 15. Alternatively, reductive etherification of α-boryl silyl ethers in the presence of BiBr$_3$ is a versatile method for preparing these substrates under non-basic conditions. Thus silyl ether 25, readily available from 6, can be condensed with isobutyraldehyde in the presence of Et$_3$SiH to yield 17. An additional benefit of the reductive annulation protocol lies in the enhanced stability of α-boryl silyl ethers in comparison to α-boryl alcohols. This allows for the substrate scope to be broadened to include aldehyde-derived boronates such as 19.

Scheme 4. Etherification in the absence of strong base.

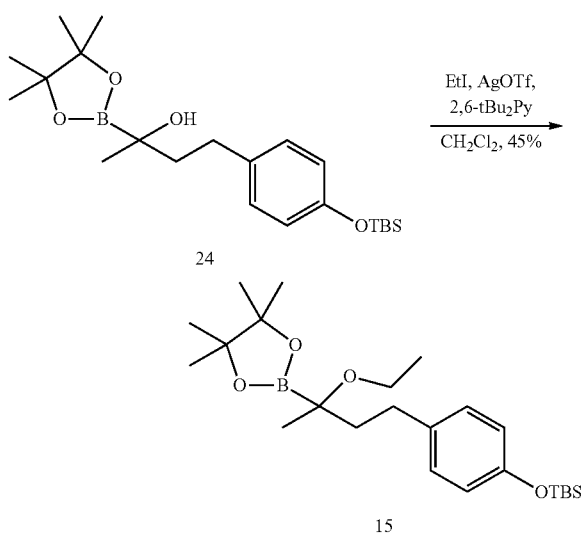

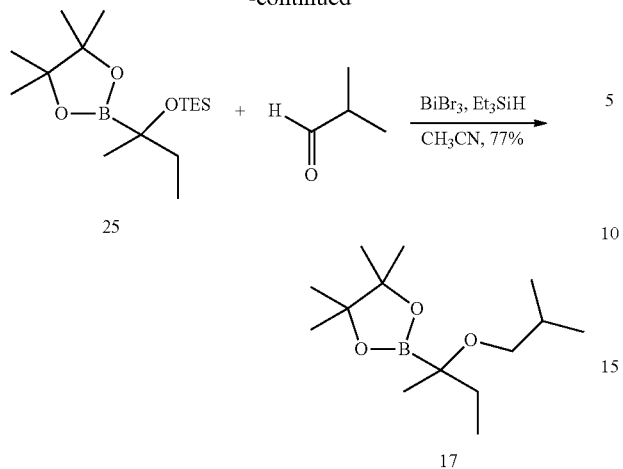

The functional group tolerance of the process and the capacity for α-boryl alcohols to add into oxocarbenium ions suggested that the scope could be expanded further to promote aldehyde and ketone release. The preparation of the substrates for these studies is illustrated in Scheme 5. Acetal substrates can be prepared either through oxidative or classical exchange reactions. Ketone 26, available from commercially available 4-hydroxy-2-butanone, underwent copper-catalyzed borylation smoothly to yield alcohol 27. DDQ-mediated oxidative cyclization provided acetal 28 in 78% yield. This acetal was formed as a single stereoisomer, with the relative configuration being determined through a NOESY experiment. Removing the PMB group from 27 under hydrogenolytic conditions followed by acetal exchange with the dimethyl acetal of benzophenone provided acetal 29 in 49% yield over two steps.

The boryl-substituted acetals release their cargo readily, as shown in Scheme 6. Boronate 28 reacted with $H_2O_2$ at pH=8.0 to provide hemiacetal 30, which broke down to form anisaldehyde and 1-hydroxy-3-butanone in 94% yield. Over 50% of the starting material was consumed within 90 sec, and complete conversion occurred in <15 min. Similarly boronate 29 reacted to form benzophenone quickly and efficiently. Therefore this variation of the protocol significantly extends the range of structures that can be released in the presence of hydrogen peroxide. Moreover this strategy illustrates a new approach to designing prodrugs for aldehydes and ketones, as previous efforts have largely centered on the use of oximes and derivatives.

Scheme 6. Aldehyde and ketone release through oxidative acetal cleavage.

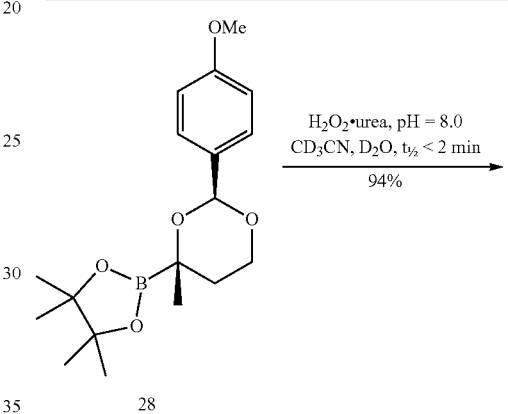

Scheme 5. Synthesis of cyclic acetal substrates.

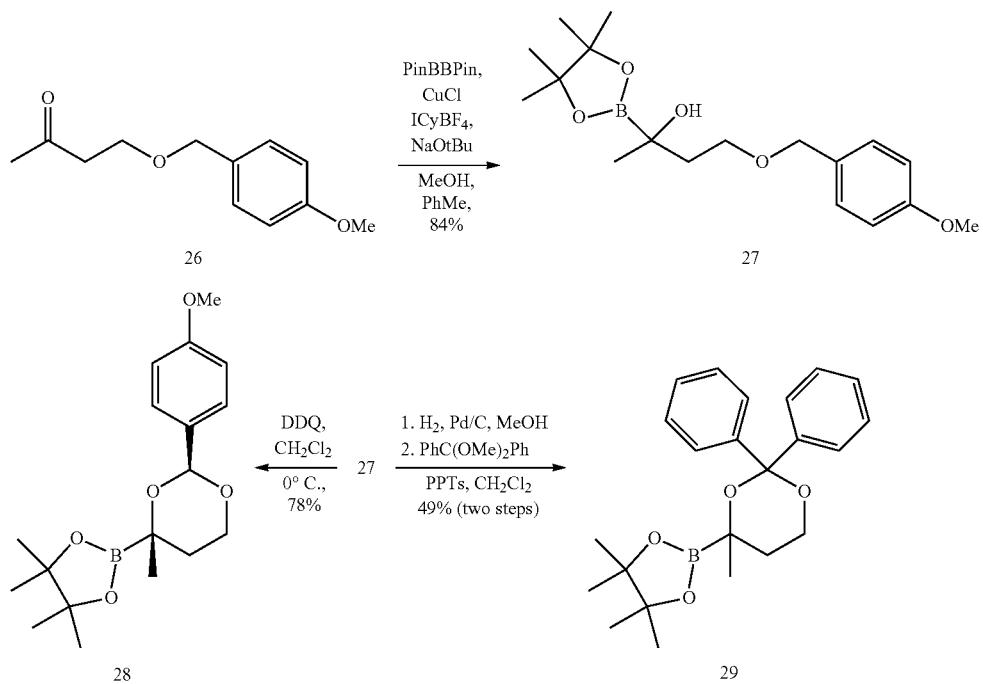

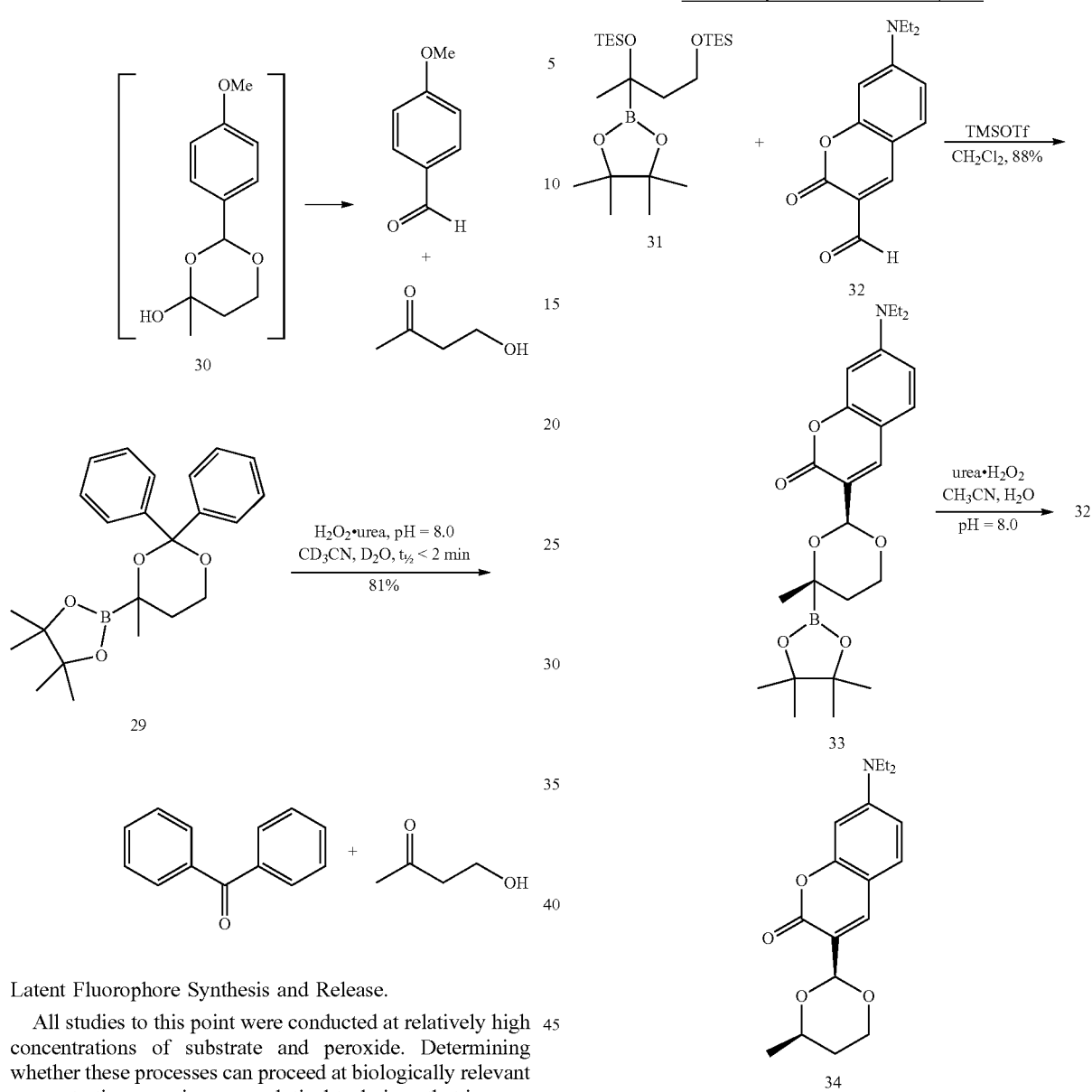

Scheme 7. Synthesis of a latent fluorophore.

Latent Fluorophore Synthesis and Release.

All studies to this point were conducted at relatively high concentrations of substrate and peroxide. Determining whether these processes can proceed at biologically relevant concentrations requires an analytical technique that is more sensitive than $^1$H NMR. Therefore we explored the potential for the release of a fluorophore at low substrate and peroxide concentrations. The synthesis of a latent fluorophore is shown in Scheme 7. Bis-silyl ether 31, which was prepared from the triethylsilyl ether of 4-hydroxy-2-butanone, coupled with adehyde 32 (prepared from commercially available materials in two steps) in the presence of TMSOTf to yield acetal 33. The Noyori acetalization conditions were significantly superior to Brønsted acid-mediated protocols due to the absence of protodeboration as a prominent competing reaction. Acetalization induces significantly different fluorescence properties relative to the aldehyde, with $\lambda_{ex}$ values of 448 nm and 402 nm and $\lambda_{em}$ values of 510 nm and 452 nm for 32 and 33, respectively, thereby facilitating the monitoring of oxidative breakdown. Acetal 34 was prepared through a similar protocol to serve as a control compound in evaluating the importance of the oxidative trigger in peroxide-mediated decomposition.

Figure 3:
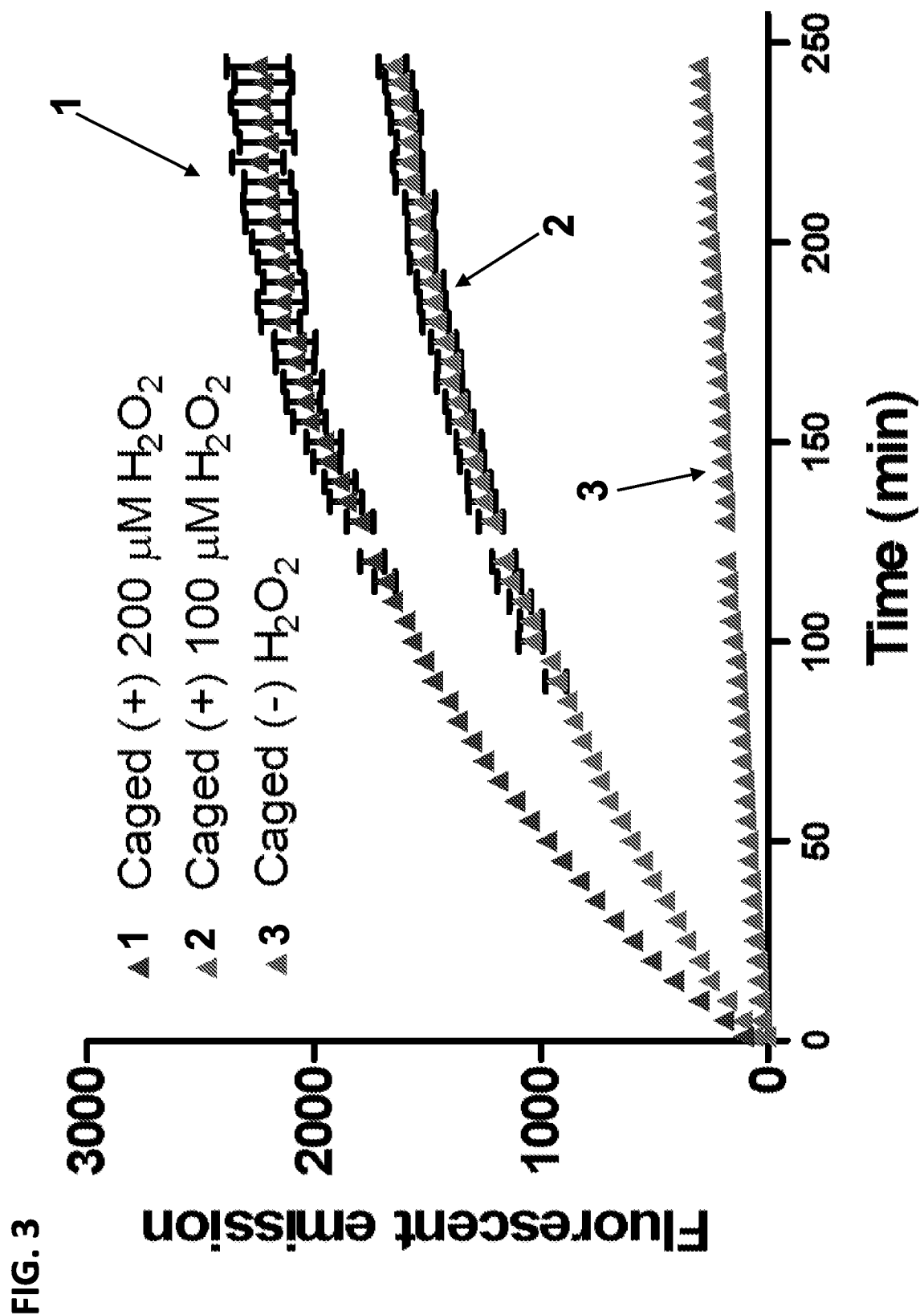
FIG. 3 is a graph demonstrating fluorophore release at low substrate and peroxide conditions.

Fluorophore release was studied at a concentration of 25 µM for 33 at pH=7.4 with $H_2O_2$ concentrations of 50 µM to 200 µM. The concentration of 32 was monitored by excitation at 448 nm and emission at 499 nm (a wavelength where 33 shows only slight emission), with product release being quantitated by comparison to a standard curve. The fluorophore release experiments are summarized in FIG. 3. The breakdown of 33 was conducted in 1% acetonitrile in aqueous phosphate buffer. Fluorophore concentration increased steadily with time. The rate and extent of fluorophore release showed the expected dependency upon $H_2O_2$ concentration. Lowering the $H_2O_2$ concentration from 200 µM to 100 µM slowed fluorophore release to a small but noteworthy extent. The yield of 32 was 88% with 200 µM $H_2O_2$ and 78% with 100 µM $H_2O_2$. Fluorophore release was minimal in the absence of $H_2O_2$. Acetal 34 did not release 32 at any $H_2O_2$ concentration over the time span of the experiment, thereby validating the importance of boronate oxidation in cargo release. Separate studies in the presence of a large excess of $H_2O_2$ (10 mM) allowed for the determination of a pseudo-first order rate constant of $1.47 \times 10^{-3}$ $sec^{-1}$. This rate compares favorably to the peroxide-mediated decomposition of boryl-substituted benzylic carbamates to generate quinone methides via 1,6-elimination. The 1,6-elimination protocol is likely to be significantly slower for releasing aliphatic alcohols, however, in consideration of their lower nucleofugacity and our prior observation that the rates of these processes are strongly correlated with the rate of benzylic C—O bond cleavage.

Figure 4:
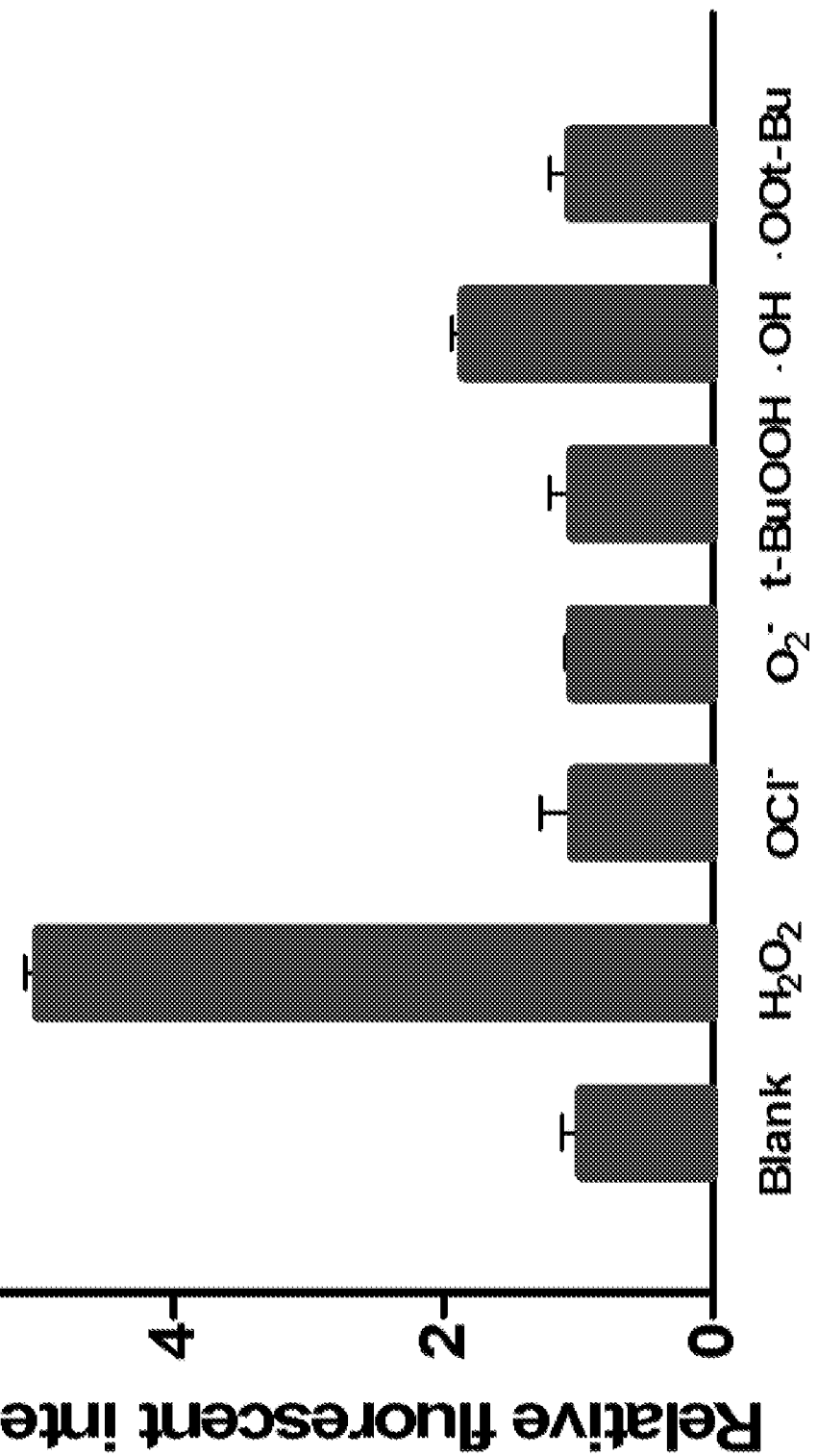
FIG. 4 is a graph showing the comparison of fluorophore release by different oxidants. $[33]_0 = 40$ μM, $[oxidant]_0 = 200$ μM, pH=7.4.
Figure 5A:
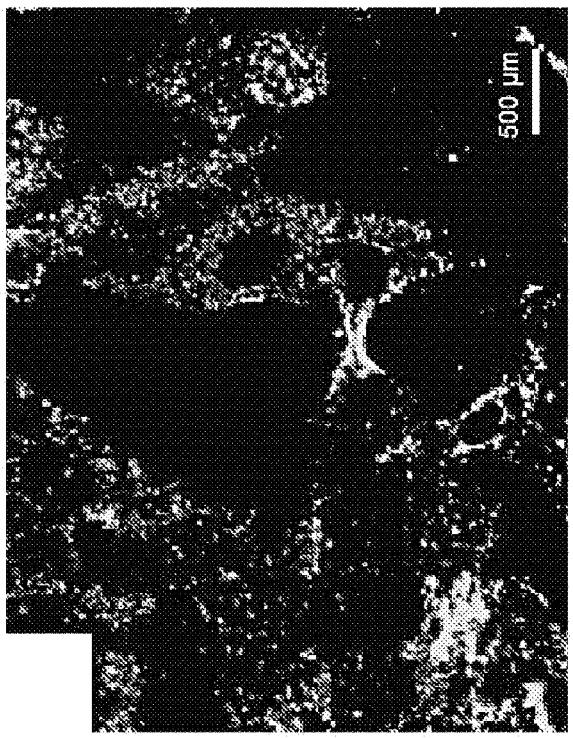
FIG. 5. Fluorophore release in HeLa cells treated with exogenous $H_2O_2$. Cells were incubated with 33 (10 μM) in DPBS buffer for 45 min at 37° C., followed by replacement with fresh DPBS containing (A) vehicle or (B) $H_2O_2$ (100 μM). After 30 min, fluorescence was imaged (Zeiss Axio Observer Z1, 20× objective, GFP filter (Set 38 HE; ex. 470 nm; em. 525 nm)). (C) Bright-field image of cells in (B) stained with Hoechst 33258 (1 μM) and imaged using a DAPI filter (Set 68; ex. 377 nm; em. 464 nm). (D) Mean fluorescence intensities were calculated from three individual HeLa cells and set relative to the mean fluorescence intensity prior to treatments ($F/F_i$). Error bars denote standard deviations, ***P<0.001.
Figure 5B:
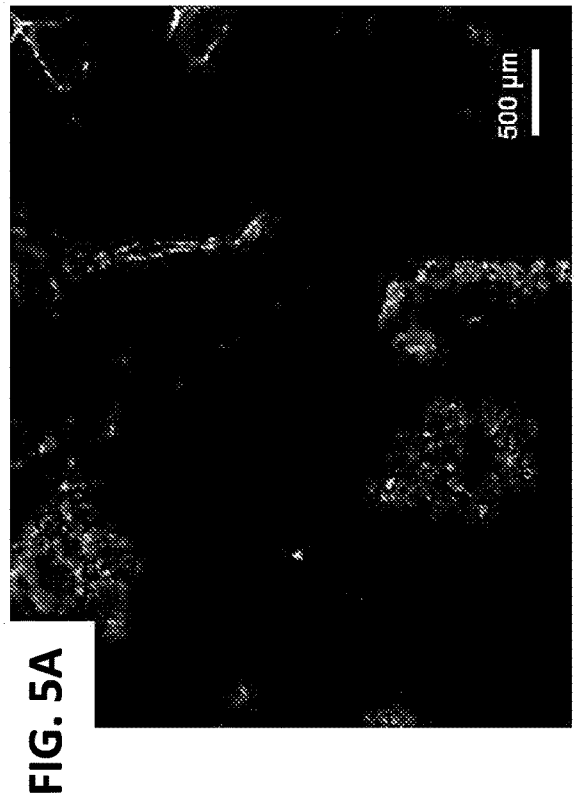
Figure 5C:
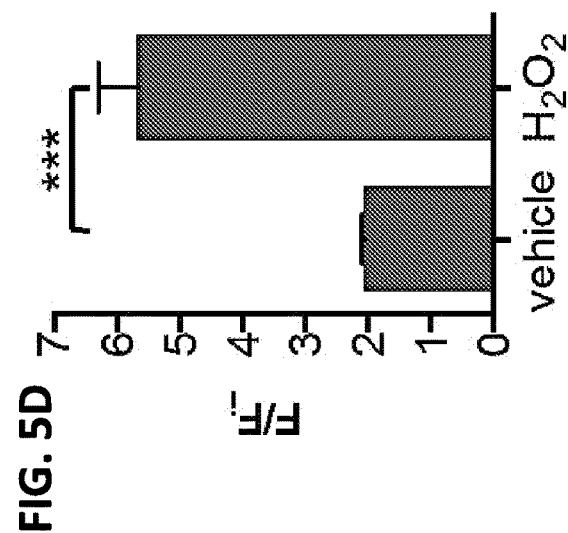
Figure 5D:
Figure 6A:
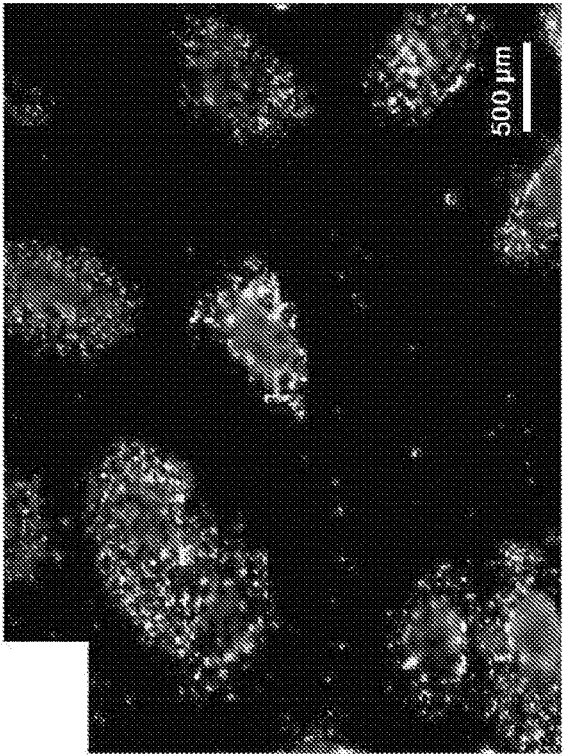
FIG. 6. Cellular fluorophore release in HeLa cells by endogenous, PMA-stimulated $H_2O_2$ generation. Cells were pre-treated in DMEM containing (A) DMSO or (B) PMA (1 uM) and incubated at 37° C. for 60 minutes. Media was replaced with fresh DPBS containing 33 (10 uM) and cells were incubated for an additional 60 min at 37° C. before fluorescence was imaged (Zeiss Axio Observer Z1, 20× objective, GFP filter (Set 38 HE; ex. 470 nm; em. 525 nm)). (C) Bright-field image of cells in (B) stained with Hoechst 33258 (1 μM) and imaged using a DAPI filter (Set 68; ex. 377 nm; em. 464 nm). (D) Mean fluorescence intensities were calculated from three individual HeLa cells and set relative to the mean fluorescence intensity prior to treatments ($F/F_i$). Error bars denote standard deviations, **P<0.01.
Figure 6B:
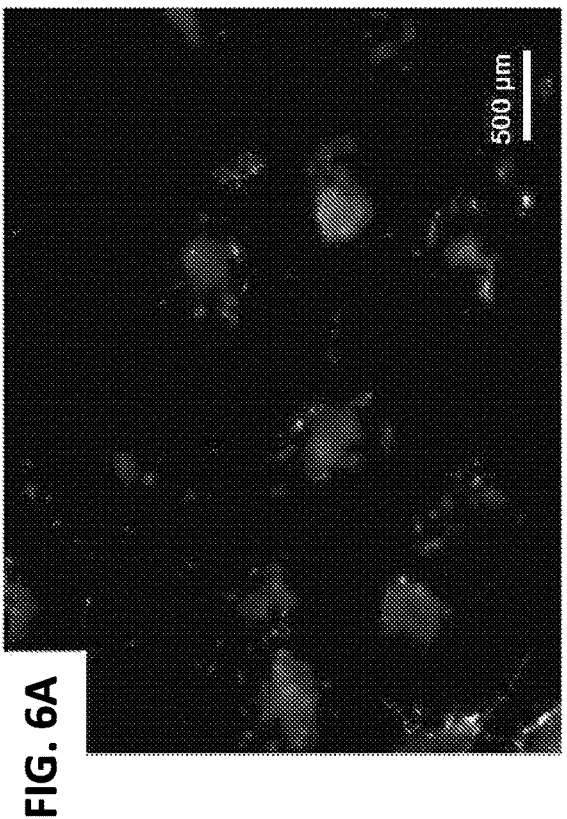
Figure 6C:
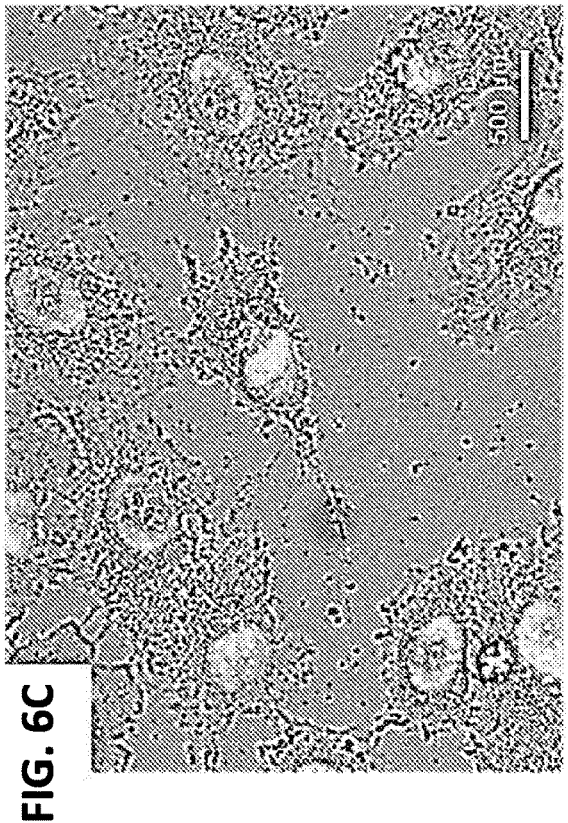
Figure 6D:
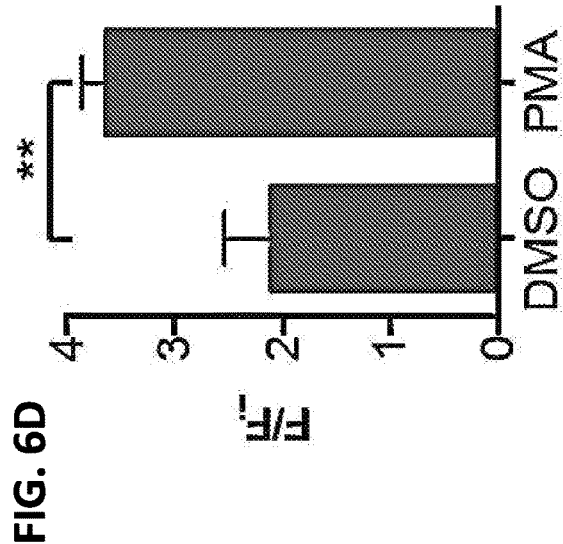
Figure 7:
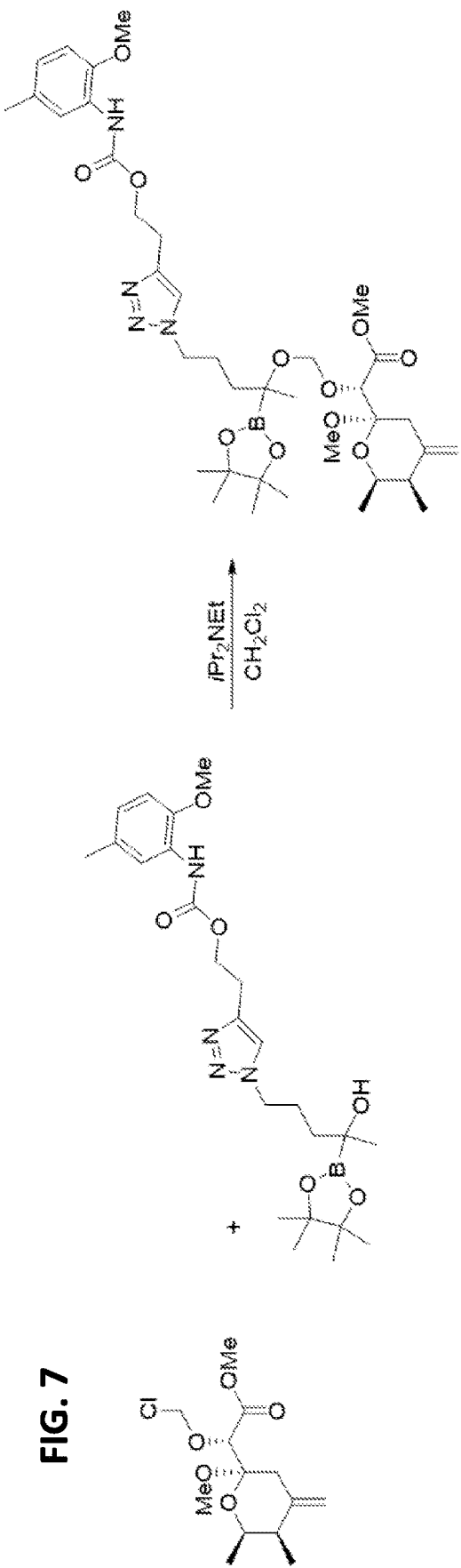
FIG. 7 depicts an example of a compound disclosed herein.
Figure 7:
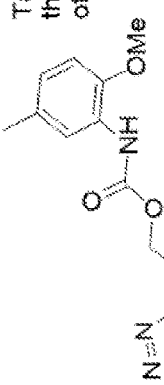
Figure 7:
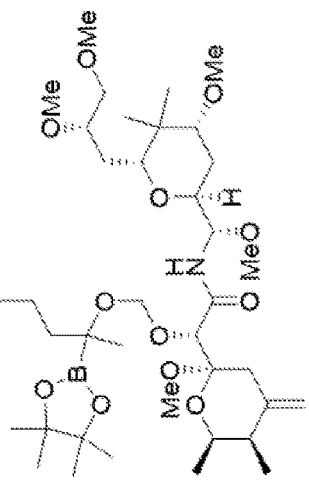

Exposing 33 to a number of reactive oxygen species showed that the breakdown is selective for $H_2O_2$ (FIG. 4). Solutions of $H_2O_2$, NaOCl, $KO_2$, and tBuOOH were prepared by diluting commercially available material. Hydroxyl and t-butoxyl radicals were prepared by mixing the corresponding peroxide with $FeSO_4 \cdot 5H_2O$ and adding catalase to consume residual peroxide. The chart shows the ratio of fluorescence intensity after 30 min to the initial value. Aside from $H_2O_2$ only hydroxyl radical showed a notable fluorophore release, albeit significantly lower in magnitude compared to $H_2O_2$-mediated release.

Cellular Fluorophore Release.

These results led us to study the release of the fluorophore in cells to provide an easily-visualized demonstration of these compounds' capacity to deliver cargo in a biologically-relevant environment. This was demonstrated in accord with Chang's protocol, whereby HeLa cells were incubated with solutions of 33 (12.5 and 25 μM) for 45 min and comparing fluorophore release in the absence and presence of exogenous 100 μM $H_2O_2$. The results are shown in FIG. 4. Very little fluorophore release occurred within 45 min in the absence of external $H_2O_2$ with the small response most likely being attributable to the endogenous peroxide that is present in cancer cells. Significant fluorophore release was observed in the presence of $H_2O_2$, however. This demonstrates that α-boryl acetals are cell-permeable and can release cargo within cells. Conducting these studies with control acetal 34 resulted in no fluorophore release, thereby providing further evidence for the proposed release mechanism.

While these studies provide compelling evidence for the capacity of α-boryl acetals to release cargo in cells, the results would have significantly more impact if fluorophore release could be achieved through endogenous $H_2O_2$ generation. Phorbol myristate acetate (PMA) promotes intracellular $H_2O_2$ generation. Therefore HeLa cells were incubated with PMA (1 μM) for 45 min followed by the addition of 34 (12.5 μM). Fluorophore release in cells that were treated with PMA showed a steady increase with time (FIG. 6), in contrast to the lack of fluorophore release in cells that were not treated with PMA. These result clearly show the capacity of α-boryl acetals to release compounds inside of cells in response to endogenous concentrations of $H_2O_2$.

We have shown that α-boryl ethers and related structures are excellent vehicles for releasing molecular cargo in an oxidative environment. These compounds are accessed from α-boryl alcohols that can be prepared by operationally facile ketone or aldehyde borylation reactions. Although these alcohols cannot be functionalized via their alkoxides, they can be alkylated or acylated in the presence of weak amine bases. Reductive alkylation provides an attractive alternative to boryl ether formation under acidic conditions. α-Boryl ethers release alcohols extremely rapidly in the presence of $H_2O_2$ while α-boryl carbonates decompose somewhat more slowly, providing a predictable mechanism for controlling the rate of alcohol release. The capacity to functionalize α-boryl alcohols under acidic conditions provides a pathway to generate α-boryl acetals. These structures readily release aldehydes and ketones upon exposure to $H_2O_2$. The ability to liberate cargo at low substrate and peroxide concentrations was validated through the release of a fluorescent aldehyde. Fluorophore release can also be achieved inside cells with exogenous $H_2O_2$ or with endogenous, chemically-stimulated $H_2O_2$ generation. The presence of the boronate group is essential to these processes, in support of the proposed pathway for the breakdown. The capacity to release molecules inside cells with a sterically non-demanding oxidant while generating non-toxic by-products indicates that these compounds will be valuable for drug release in oxidatively stressed cells.

In view of the many possible embodiments to which the principles of the disclosed invention may be applied, it should be recognized that the illustrated embodiments are only preferred examples of the invention and should not be taken as limiting the scope of the invention.

What is claimed is:

1. A compound, or a pharmaceutically acceptable salt thereof, having a structure of:

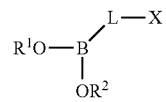

wherein L is a cleavable linker group;

X is a cargo moiety-containing group; and $R^1$ and $R^2$ are each independently hydrogen, alkyl, or substituted alkyl; or $R^1$ and $R^2$ together form a boronic ester ring or a substituted boronic ester group;

wherein L is:

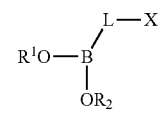

wherein $R^5$, $R^6$, and $R^7$ are each independently selected from hydrogen, alkyl, substituted alkyl, thiol or substituted thiol, or a targeting moiety.

2. The compound of claim 1, wherein L is selected from:

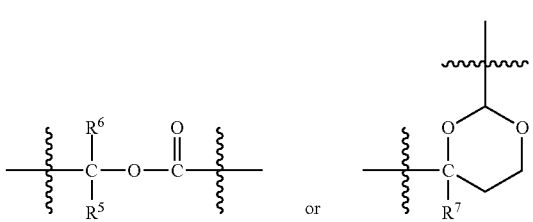

3. The compound of claim 1, wherein the —B(OR$^1$)(OR$^2$) group is selected from the following:

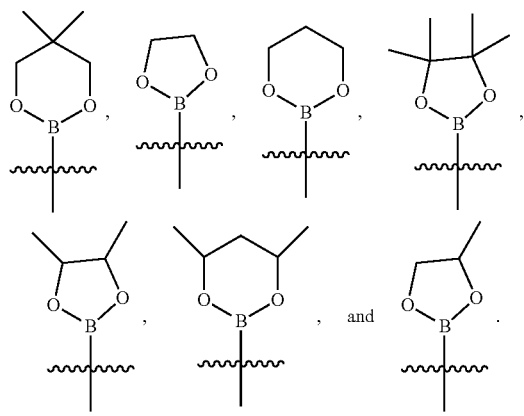

4. The compound of claim 1, wherein X includes a therapeutically active moiety.

5. The compound of claim 1, wherein X includes a detectable moiety.

6. The compound of claim 4, wherein the therapeutically active moiety is an anticancer agent, a neurological agent, or an antioxidant.

7. The compound of claim 1, wherein at least one of R$^5$, R$^6$, or R$^7$ includes a targeting moiety.

8. The compound of claim 1, wherein X includes a targeting moiety.

9. The compound of claim 7, wherein the targeting moiety targets a cell.

10. The compound of claim 1, wherein L is configured to undergo cleavage upon reaction of the compound with a reactive oxygen species.

11. The compound of claim 10, wherein the reactive oxygen species is hydrogen peroxide.

12. The compound of claim 11, wherein the hydrogen peroxide is endogenous hydrogen peroxide within a cell within a subject.

13. The compound of claim 11, wherein the hydrogen peroxide is exogenous hydrogen peroxide provided or generated within a cell within a subject.

14. The compound of claim 4, wherein the therapeutically active moiety is an anticancer agent.

15. The compound of claim 14, wherein the therapeutically active moiety is paclitaxel.

16. The compound of claim 1, wherein L is:

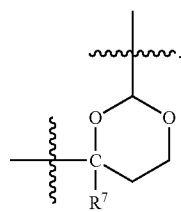

17. The compound of claim 4, wherein the therapeutically active moiety is paclitaxel.

18. A compound, or a pharmaceutically acceptable salt thereof, having a structure of:

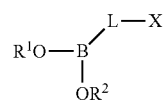

wherein L is a cleavable linker group that includes an —O—, —C(O)—, or —O—C(O)—O—, and L includes a targeting moiety;

X is a cargo moiety-containing group; and the —B(OR$^1$)(OR$^2$) group is selected from the following:

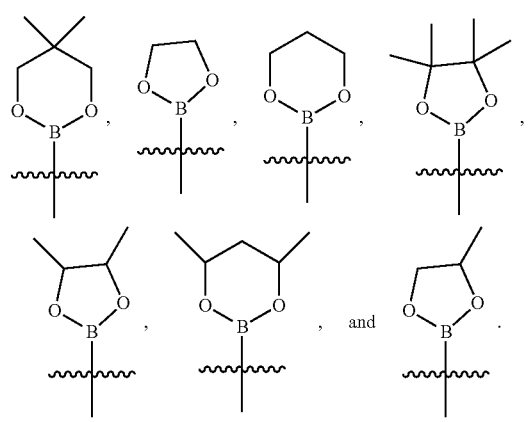

19. The compound of claim 18, wherein X includes a therapeutically active moiety.

20. The compound of claim 19, wherein the therapeutically active moiety is an anticancer agent, a neurological agent, or an antioxidant.

21. The compound of claim 18, wherein L is configured to undergo cleavage upon reaction of the compound with a reactive oxygen species.

22. The compound of claim 21, wherein the reactive oxygen species is hydrogen peroxide.

23. A compound, or a pharmaceutically acceptable salt thereof, having a structure of:

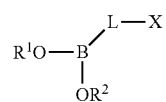

wherein L is a cleavable linker group;

X is a cargo moiety-containing group; and the —B(OR$^1$)(OR$^2$) group is selected from the following:

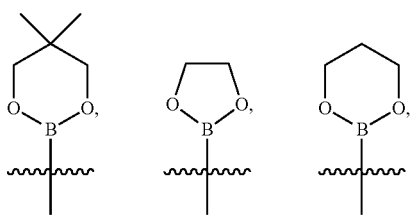

-continued

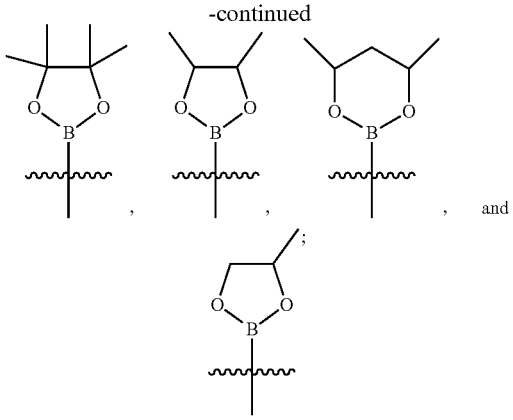

wherein L is selected from:

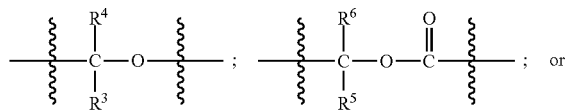

-continued

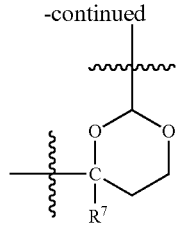

wherein $R^3$-$R^7$ are each independently selected from hydrogen, alkyl, substituted alkyl, thiol or substituted thiol, or a targeting moiety, provided at least one of $R^3$-$R^7$ includes a targeting moiety.

24. The compound of claim 23, wherein X includes a therapeutically active moiety.

25. The compound of claim 24, wherein the therapeutically active moiety is an anticancer agent, a neurological agent, or an antioxidant.

26. The compound of claim 23, wherein L is configured to undergo cleavage upon reaction of the compound with a reactive oxygen species.

27. The compound of claim 26, wherein the reactive oxygen species is hydrogen peroxide.

* * * * *